United States Patent [19]

Cripps et al.

[11] Patent Number: 6,068,985

[45] Date of Patent: *May 30, 2000

[54] IN VITRO TEST FOR *HELICOBACTER PYLORI*

[75] Inventors: Allan Cripps, Curtin; Campbell Witt, Bicton; Robert Llewellyn Clancy, Newcastle; Daniel Stiel, East Lindfield, all of Australia

[73] Assignee: Provalis UK Limited, Deeside, United Kingdom

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/325,264

[22] PCT Filed: Apr. 29, 1993

[86] PCT No.: PCT/GB93/00894

§ 371 Date: Apr. 26, 1995

§ 102(e) Date: Apr. 26, 1995

[87] PCT Pub. No.: WO93/22682

PCT Pub. Date: Nov. 11, 1993

[30] Foreign Application Priority Data

Apr. 29, 1992 [CA] Canada .................................. 2067603

[51] Int. Cl.[7] ................................................. G01N 33/554
[52] U.S. Cl. ....................................... 435/7.32; 424/234.1
[58] Field of Search .............................. 435/7, 7.32, 12; 514/78; 424/92; 536/23.1; 128/760

[56] References Cited

U.S. PATENT DOCUMENTS

| | | | |
|---|---|---|---|
| Re. 34,101 | 10/1992 | Evans et al. | 435/7.32 |
| 4,882,271 | 11/1989 | Evans et al. | 436/7 |
| 5,200,344 | 4/1993 | Blaser | 435/7.32 |
| 5,262,156 | 11/1993 | Alemohammad | 424/92 |
| 5,314,804 | 5/1994 | Boguslaski et al. | 435/12 |
| 5,339,829 | 8/1994 | Thieme et al. | 128/760 |
| 5,403,924 | 4/1995 | Cover et al. | 536/23.1 |
| 5,411,948 | 5/1995 | Lingwood et al. | 514/78 |
| 5,420,014 | 5/1995 | Cripps et al. | 435/7.32 |
| 5,420,016 | 5/1995 | Boguslaski et al. | 435/12 |
| 5,439,801 | 8/1995 | Jackson | 435/12 |
| 5,610,286 | 3/1997 | Shau et al. | 536/23.5 |

FOREIGN PATENT DOCUMENTS

| | | |
|---|---|---|
| 67676 | 6/1991 | Australia . |
| 67676/90 | 6/1991 | Australia . |
| 6767690 | 6/1991 | Australia . |
| 0329570 | of 1989 | European Pat. Off. . |
| 89/08843 | 9/1989 | WIPO ........................................ 33/53 |
| 90/03575 | 4/1990 | WIPO . |

OTHER PUBLICATIONS

S. Czinn et al., "Digestive Disease Week And The 90th Annual Meeting of The American Gastroenterological Association", *Gastroenterology*, vol. 96, No. 5, Part 2, (1989).

B. E. Dunn et al., "Two–Dimensional Gel Electrophoresis And Immunoblotting Of *Campylobacter Pylori* Proteins", *Infection And Immunity*, vol. 57, No. 6, pp. 1825–1833, (1989).

Evans et al., "A Sensitive and Specific Serologic Test for Dectection of *Campylobacter pylori* Infection", Gastroenterology, 96, 1989, pp. 1004–1008.

Witt et al., "Salivary Antibodies in the Diagnosis of *Helicobacter Pylori* infection", Elsevier, Sci. Publ., vol. 1, 1991, pp. 693–696.

Schaber et al., "Indirect Immunofluorescence Test and Enzyme–Linked Immunosorbent Assay for Detection of *Campylobacter pylori*", Journ. Clin. Microbio., vol. 27, No. 2, 1989, pp. 327–330.

Loffeld et al., "Diagnostic Value of an Immunoassay to Detect Anti *Campylobacter Pylori* Antibodies in No–Ulcer Dyspepsia", Lancet, 1989, pp. 1182–1185.

Pateraki, E. et al, FEMS Microbiol. Immunol. vol. 64, pp. 129–136, 1990.

Dunn, B.E. et al, Jun. 5, 1990, vol. 265, (16), pp. 9464–9469.

Mobley et al, International Workshop at Deerhurst, Huntsville, Ontario, CA, Feb. 21–24, 1991.

Casareo, S.D. et al, FEMS Microbiol. Letters, vol. 99, (No. 1, pp. 15–22, 1992.

Ferrero, R.L. et al, Microbial Eco. Health Dis, vol. 4, pp. 121–134, 1991.

Faulde, M. et al, Electrophosesis, vol. 14, pp, 945–951, 1993, pp. 945–951.

O'Toole, P.W et al, J of Bacteriol, Jan. 1991, vol. 173(2), pp. 505–513.

S. Czinn et al., Antibody Response to *Campylobacter Pylori* (*C. pylori*)—A comparison of the Systemic and Mucosal immune System, Gastroenterology; May 13–19, 1989, Washington D.C.

Owens et al, J App. Bacter., 1989, vol. 66, pp. 331–337.

*Primary Examiner*—James C. Housel
*Assistant Examiner*—Ginny Allen Portner
*Attorney, Agent, or Firm*—Foley & Lardner

[57] ABSTRACT

Contemporary infection by *Helicobacter pylori* in a human or other mammal can be detected by detecting *H. pylori*-specific IgG antibody in saliva, or other mucous secretion, with an antigen preparation from *H. pylori*. Diagnosis depends on detection of the antigen-antibody complex. For improved reliability, the antigen preparation comprises *H. pylori*-derived components of about 265 kDa and about 340 kDa and is substantially free of an *H. pylori*-derived component of about 440 kDa. The antigen preparation may be immobilised onto a solid support such as a nitrocellulose strip.

20 Claims, No Drawings

IN VITRO TEST FOR *HELICOBACTER PYLORI*

This is a national stage application under 371 and claims priority to PCT/GB93/00894, filed Apr. 29, 1993.

The present invention relates generally to a method and kit which permit the rapid in vitro detection of *Helicobacter pylori* infection in mammals. More particularly, the present invention contemplates a method for the detection of IgG antibodies against *H. pyloni* in mucous secretions and thereby provides a means to monitor contemporary infection by the microbe in mammals.

Gut infections in mammals, and in particular humans, stimulate an immune response in mucous secretions, such as saliva, through activation of the common mucosal immune system. This response often initially parallels an antibody response in serum although is generally characterised by the presence of IgA antibodies. However, the immune response in secretion, including saliva, rapidly diminishes following elimination of the antigen (eg bacteria or virus) from the body. Accordingly, the presence of antibody in mucous secretions reflects current, ie contemporary, infection. In the case of a microbial infection, for example, antibodies in mucous secretions, hereinafter referred to as secretious antibodies, reflect the current status of colonisation of the microbe, such as in the gut, and thus is a useful monitor of contemporary infection. Serum antibody, on the other hand, persists for some time after the microbe is eliminated from the body. A positive serum antibody test, therefore, reflects both past and present exposure to antigen which is less helpful to the clinician. A positive secretious antibody test, on the other hand, indicates present or contemporary infection by the microbe.

The present invention arose following an investigation into *Helicobacter pylori* (also known as *Campylobacter pylori*) infection in the gut of mammals. The diagnosis of *H. pylori* infection can be made by microscopy, microbiological culture or urease detection in gastric mucosal biopsies, urea breath test or by the presence of specific antibodies in serum ELISAs. It might be predicted that *H. pylori* infection, being an infection of the gastric mucosa, would elicit an IgA antibody response in gastric secretion. However during work prior to the present invention, it was discovered that *H. pylori*-specific antibody in mucous secretions is of the IgG class and not IgA as might have been expected. Little IgA antibody, if any, is detected. Accordingly, AU-A-9067676 is directed to the detection of IgG in mucous secretion specific to *H. pylori* antigen and thereby provides a means of monitoring current, ie contemporary, infection by that microorganism in mammals. The corresponding academic publication is Witt et al, *Frontiers in Mucosal Immunology* 1 693–696 (1991).

The presence of IgG antibodies in the saliva of *Campylobacter pylori* positive patients has received some attention in the proceedings of the Annual Meetings of the American Gastroenterological Association. After the disclosure by Czinn et al of the presence of such antibodies in the 1989 proceedings, Larsen et al concluded in the May 1991 proceedings that salivary IgG levels are a practical, non-invasive marker of therapeutic response during a course of antibiotic therapy. In the April 1992 proceedings, Landes et al confirmed earlier observations and observed that measurement of salivary IgG to *Helicobacter pylori* is a simple, non-invasive test for detecting *H. pylori* positive patients, especially in widespread or paediatric populations where other tests are not practical.

It is clear from the above that there is widespread interest in, and clinical potential for, a salivary IgG based diagnostic test for *H. pylori*. Equally, it is clear that such a test must be reliable as well as convenient. Invasive techniques are known (eg from U.S. Pat. No. 4,882,271, Schaber et al, *J. Clin. Microbiol.* 27(2) 327–330 (1989), Loffeld et al, *The Lancet*, May 27, 1989, 1182–1185 and Evans et al, *Gastroenterology* 96 1004–1008 (1989)) and established (eg the CLOTEST™ kit which is available from Delta West Ltd, Perth, Western Australia and which detects the presence of urease in biopsy samples). A non-invasive test must rival the reliability of invasive tests for it to become accepted and useful.

The present invention relates to improving the reliability of saliva-based (and other mucous-based) IgG tests for *H. pylori*. It has been found that the immunological specificity of the test method can be improved by detecting mucous IgG by using certain antigens from *H. pylori* and by avoiding the use of another.

According to a first aspect of the present invention, there is provided a method for detecting contemporary infection by *Helicobacter pylori* in a mammal, the method comprising contacting a mucous secretion from the mammal with an antigen preparation from *H. pylori* for a time and under conditions sufficient for an IgG antibody in the mucous secretion specific to the antigen component to form a complex therewith and then subjecting the complex to a detecting means in order to detect the complex, wherein the antigen preparation comprises an *H. pylori*-derived component of about 265 kDa and is substantially free of an *H. pylori*-derived component of about 440 kDa.

The present invention thus provides an effective in vitro assay for *H. pylori* infection by screening for IgG antibodies in mucous secretions.

It has been found that if the ca. 440 kDa component is present, false positives can occur in certain patients. If the ca. 265 kDa antigen is absent false negatives may occur. Additionally, if a ca. 340 kDa antigen derived from *H. pylori* is not present, false negatives may occur in certain patients; the presence of the ca. 340 kDa antigen is therefore highly preferred. Other antigen components from *H. pylori* which may, but do not have to be, present include those with molecular weights of about 160 kDa and about 70 kDa.

An antigen component is present, for the purposes of this invention, if it is detectable by Western blot analysis. Conversely, it is absent if it is not detectable by this means. The usually accepted sensitivity of Western blot analysis is in the order of 20 $\mu$g/ml.

Molecular weights of antigen components useful in the present invention are of necessity approximate figures, because of the limitations of current molecular weight determination procedures. The molecular weights specifically referred to have been obtained by a native polyacrylamide gel electrophoresis (PAGE) system sold by Pharmacia under the trademarks PHASTGEL™ and PHASTSYSTEM™ using the PHASTGEL gradient 8–25. This system gives a linear relationship between a protein's migration distance and the logarithm of its molecular weight for the molecular weight range 50,000 to 750,000 for globular proteins. Pharmacia provide a set of high molecular weight markers in their electrophoresis calibration kit; this marker set was used to calibrate the gels referred to in this specification. Those skilled in the art will be aware that slightly different results can be obtained in different hands or even on different occasions in the same hands, and so the approximate molecular weight figures quoted in this specification should be read as ±5% or even ±10%. For this reason the ca. 265 kDa antigen is sometimes referred to as the 255–275 kDa antigen.

The expression "antigen" is used in its broadest sense and includes whole *H. pylori* cells or homogeneous, near homogeneous or heterogeneous extracts from *H. pylori*, all of which are capable of binding to specific antibody in a mucous secretion; providing always that ca. 265 kDa (and preferably ca. 340 kDa) *H. pylori*-derived antigens are present and a ca. 440 kDa *H. pylori*-derived antigen is substantially absent. Antigen components contemplated by the present invention include protein, polysaccharide or lipid or any combination thereof. Preferably, the antigen is protein, lipopolysaccharide or cell extract of *H. pylori* prepared by, for example, sonication, pressure disintegration, detergent extraction or fractionation.

One of the most effective methods of ensuring that the necessary antigens are present, while removing many irrelevant components, is the use of chromatography on crude extracts (for example sonicatds) of *H. pylori* cells. For example, fast protein liquid chromatography (FPLC), such as using a SUPEROSE™ 6 size exclusion column, is particularly effective when applied to a crude sonicate of cells which has been subjected to ion-exchange chromatography. Other methods will be well within the abilities of those skilled in the art.

Correspondingly, one of the most effective methods of ensuring that the unwanted ca. 440 kDa antigen is absent is the use of freeze drying on an extract of *H. pylori* cells, particularly after chromatographic purification such as FPLC. Freeze drying may be carried out in any suitable apparatus for the purpose. The actual equipment and conditions used will depend on the scale of the preparation. It is preferred that the freeze drying process is carried out substantially to completion, within the limits of the equipment used.

The invention extends to the use of naturally occurring form of antigens and to synthetic (eg recombinant) forms and immunologically active derivatives, analogues and relatives thereof. It is therefore clear that an effective antigen set for use in the present invention can either be selectively stripped down from an *H. pylori* cell preparation or built up from individual components or mixtures of components.

In the method of the invention, antibody is detected in mucous secretion. By "mucous secretion" is meant the secretion from mucous-secreting epithelial cells (ie mucous membrane) such as those which line the canals, cavities and tracts that communication with the external air, and in particular the nose, throat, respiratory tract, eyes, genital and urinary passages and the digestive system. In preferred embodiments, the mucous secretion is nasal secretion, sputum or, particularly, saliva.

The saliva or other mucous secretion may be assayed undiluted or diluted with an appropriate diluent (such as distilled water). with increasing sensitivities, dilution may be preferred (particularly when collection devices are used).

The antigen preparation will for convenience and preference be bound to a solid support. Suitable solid supports include a nitrocellulose membrane, glass or a polymer. The most commonly used polymers for this purpose are cellulose, polyacrylamide, nylon, polystyrene, polyvinyl chloride or polypropylene, but the invention is not limited to them. The solid supports may be in the form of strips, tubes, beads, discs or microplates, or any other surface suitable for conducting an immunoassay.

Antigen components of *H. pylori* useful in this invention may be either covalently or non-covalently ("passively") bound to the solid surface. Suitable binding processes are well known in the art and generally consist of cross-linking, covalently binding or physically adsorbing the antigen to the solid support.

Infection is diagnosed by means of the present invention by detecting the formation of a complex between IgG antibody in a mucous sample and *H. pylori* antigens. Some form of detecting means is therefore necessary to identify the presence (or, if required, amount) of the antibody-antigen complex.

The detection means may be a second antibody, conjugated with a reporter molecule, and which is specific for at least part of the class of *H. pylori*-specific antibody found in the secretion; as explained above, that antibody is IgG.

A "reporter molecule" is a molecule or group which, by its chemical nature, has an analytically identifiable characteristic or provides an analytically identifiable signal which allows the detection of antigen-bound antibody. Detection may be either qualitative or quantitative. The most commonly used reporter molecules in this type of assay are either enzymes, fluorophores or radionuclide containing molecules (ie radioisotopes). In the case of an enzyme immunoassay, an enzyme is conjugated to the second antibody, generally by means of glutaraldehyde or periodate. As will be readily recognised, however, a wide variety of different conjugation techniques exist, which are readily available to those skilled in the art. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable colour change. Substrates can be soluble or insoluble, depending upon the chosen application. For example, 5-bromo-4-chloro-3-indolyl phosphate/nitroblue tetrazolium is suitable for use with alkaline phosphatase conjugates; for peroxidase conjugates, 1,2-phenylenediamine-5-aminosalicylic acid, 3,3,5,5-tetramethylbenzidine, tolidine or dianisidine are commonly used. It is also possible to employ fluorogenic substrates, which yield a fluorescent product, rather than the chromogenic substrates noted above. Examples of fluorogenic substrates are fluorescein and rhodamine. When activated by illumination with light of a particular wavelength, the fluorochrome-labelled antibody absorbs the light energy, inducing a state of excitability in the molecule, followed by emission of the light at a characteristic colour which is usually visually detectable with a light microscope. Immunofluorescence and EIA techniques are both well established in the art and are particularly preferred for the present method. However, other reporter molecules, such as radioisotope, chemiluminescent, and bioluminescent molecules and/or dyes and other chromogenic substances, may also be employed.

The choice of a particular reporter molecule conjugated antibody will be, for the most part, determined by the intended use and user of the present invention. Additionally, although the test is appropriate for all mammals susceptible to *H. pylori* infections, it is most applicable and useful to monitoring *H. pylori* infection in humans.

Accordingly, in a preferred embodiment, the present invention provides a method for detecting contemporary infection by *H. pylori* in a human comprising:

(a) contacting a mucous secretion from the human with an antigen preparation of *H. pylori* immobilised onto a solid support for a time and under conditions sufficient for IgG antibody in the mucous secretion specific to antigen in the antigen preparation to form a complex therewith, wherein the antigen preparation comprises *H. pylori*-derived components of about 265 kDa and about 340 kDa and is substantially free of an *H. pylori*-derived component of about 440 kDa;

(b) contacting the complex with an effective amount of a second antibody labelled with a reporter molecule and specific to the *H. pylori*-specific IgG antibody; and (c) detecting binding of the second antibody to said IgG antibody by the reporter molecule.

Hence, a medical practitioner, clinician, nurse or even patient may use a nitrocellulose or other suitable solid phase support membrane strip carrying immobilised *H. pylori* antigens, such as freeze dried, FPLC-fractionated soluble sonicate. The strip is then contacted with the mucous secretion for a time and under conditions sufficient to allow potential *H. pylori* specific antibodies of the IgG class in saliva to bind to the immobilised antigens. Instead of saliva, the source of mucous secretion may be nasal secretion or sputum.

The test strip, once exposed to mucous secretion, is then allowed to come into contact with a second antibody conjugated with a reporter molecule for a time and under conditions sufficient for the second antibody to bind to the first antibody. Preferably, the reporter molecule is an enzyme, such as alkaline phosphatase. The test strip is then washed and a substrate for the reporter molecule, (in the case where the reporter molecule is alkaline phosphatase, 5-bromo-4-chloro-3-indolyl phosphate/nitroblue tetrazolium), is brought into contact with the strip. The substrate reacts with the reporter molecule, thereby giving a detectable change. For example, alkaline phosphatase hydrolyses 5-bromo-4-chloro-3-indolyl phosphate to a purple product. This entire procedure can occur in the medical practitioner's surgery or office.

When a more quantitative enzyme-linked immunosorbent assay (ELISA) is required, such as in a clinical laboratory, a microtitre tray may be used carrying immobilised *H. pylori* antigens in the wells of the tray. In this case, samples of mucous secretion, eg saliva, are added to the well to allow potential *H. pylori*-specific IgG antibodies to bind to the immobilised antigen. Excess secretion is washed away and a second antibody specific to IgG conjugated to a reporter molecule is added to allow an antigen-antibody-conjugated antibody complex to form. This complex is detected by adding a substrate to the reporter molecule as described above to allow, for example, a visual signal which may then be quantitated spectrophotometrically or by other means.

The invention may be embodied, alternatively or additionally in an immunoblot system, which may also be quantitative (for example by measuring intensity of colour of the blot and/or distance migrated through a chromatographic strip.

The present invention, especially when in the form of the nitrocellulose strip, has many advantages over the present commercially available assays for *H. pylori*. The use of mucous secretion, and in particular saliva, to assay for *H. pylori* antibody enables diagnosis of current or contemporary infection and thus enables the medical practitioner to:

a) Link gut symptoms with *H. pylori* which would enable decisions to be made with respect to further investigation (including invasive procedures) and/or management (eg use of specific anti-*H. pylori* agents). The latter may be expected to have special significance with respect to *H. pylori*-associated non-ulcer dyspepsia, gastritis, duodenal ulceration, gastric ulceration and related and other conditions.

b) Have for the first time a convenient non-invasive test in the doctor's room, clinic or hospital to follow patients with proven peptic ulcer to detect early recurrence. A positive test enables early diagnosis and prevention or early treatment of recurrent peptic ulcer. A negative test has a reciprocal usefulness in analysis of the diagnostic approach to dyspepsia.

Additionally, the test contemplated by the present invention provides a simple yes/no answer, not requiring, for example, the taking of blood. It can be read in minutes and developed without any special preparation of specimen by the clinician. A significant advantage of the present invention is the use of mucous secretion (eg saliva) to test for antibodies specific to *H. pylori*.

According to a second aspect of the present invention, there is provided a test kit for detecting *H. pylori* in mucous secretion of a mammal, said test kit comprising (a) a solid support having an antigen preparation of *H. pylori* immobilised thereon, wherein the antigen preparation comprises *H. pylori*-derived components of about 265 kDa and about 340 kDa and is substantially free of an *H. pylori*-derived component of about 440 kDa; and (b) detection means which in use detect whether IgG in the said mucous secretion binds to one or more components of the antigen preparation.

The detection means may be an antibody conjugated with a reporter molecule which is capable of producing or giving rise to a detectable signal; the antibody would be specific against IgG antibody of the mammal in question. In a preferred embodiment, the reporter molecule is an enzyme capable of catalysing a reaction in which the product(s) is or are detectably different from the reactants). In such a case, a substrate for the enzyme, which may for example have different calorimetric properties from the product of the enzyme, will usually also be present in the kit.

Hence, in a preferred embodiment, the present invention extends to a kit for detecting *H. pylori*-specific IgG antibody in mucous secretions in a mammal, such as a human, the test kit being in compartment form and comprising:

(a) a first compartment adapted to contain a solid support having an antigen preparation of *H. pylori* immobilised thereon, wherein the antigen preparation comprises *H. pylori*-derived components of about 265 kDa and about 340 kDa and is substantially free of an *H. pylori*-derived component of about 440 kDa;

(b) a second compartment containing an antibody conjugated with a reporter molecule capable of producing a signal, the antibody being specific against IgG antibody; and (c) when the reporter molecule is an enzyme, a third compartment containing a substrate for said enzyme.

The kit may also contain additional compartments such as to receive suitable mucous material and/or for one or more diluents and/or buffers. The kit may also be packaged for sale in a suitable form.

The combination of the ca. 265 kDa and ca. 340 kDa antigens in the absence of the ca. 440 kDa antigen from *H. pylori* is useful in practising the method of the first aspect of the invention and in the preparation of kits in accordance with the second aspect of the invention. According to a third aspect of the invention, therefore, there is provided an *H. pylori* antigen preparation comprising *H. pylori*-derived components of about 265 kDa and about 340 kDa and being substantially free of an *H. pylori*-derived component of about 440 kDa.

Such an antigen preparation can be prepared, as previously indicated, by freeze-drying an extract of *H. pylori* cells to remove the ca. 440 kDa antigen. According to a fourth aspect of the invention, therefore, there is provided a process for the preparation of an antigen preparation as described above, the process comprising freeze-drying an extract of *H. pylori* cells. The extract which is subjected to freeze drying is preferably a ca. 67 kDa to ca. 440 kDa fraction obtainable by size exclusion chromatography of a crude *H. pylori* extract.

Other preferred features of each aspect of the invention are as for the other aspects, mutatis mutandis.

The following examples illustrate the invention but do not limit its scope.

EXAMPLE 1

In this example, a crude sonicate of *H. pylori* is prepared, subjected to FPLC fractionation and freeze-dried. Western blot analysis shows that approximately 265 and 340 kDa proteins are responsible factors in the immunological specificity of the assay of the present invention. These proteins only show reactivity in true positives unlike a potentially contaminating 440 kDa protein. This protein is removed by freeze-drying, to which it appears to be sensitive.

Preparation of *Helicobacter pylori* antigen

Centrifuged Sonicate, including Anion Exchange Chromatocraphy i) Cultures of *H. pylori* are harvested from chocolate agar plates in PBS. The bacteria are grown as two separate cultures, a wild strain designated "Traub" and an NCTC strain 11637.

ii) The bacteria are washed three times in PBS by centrifugation for 5 minutes at 10,000×g.

iii) Washed bacteria are resuspended in 2 ml of PBS and CFUs are estimated by reading on a spectrophotometer at 405 nm.

iv) The suspension is subjected to 5 cycles of sonication (30 seconds at 6 $\mu$, followed by 60 seconds rest which constitutes one cycle).

v) Sonicated organisms are centrifuged for 10 minutes at 10,000×g.

vi) The supernatant is recovered and filtered through a 0.45 $\mu$m filter, then a 0.22 $\mu$m filter, to remove any remaining cellular debris.

vii) After filtering, a protein estimation is performed. Note: If it is not possible to process the sonicate directly, it may be frozen down at $-70°$ C. at this point in the method until an opportunity arises to continue the method.

viii) The MONO Q™ anion exchange column can take 20–50 mg of protein per 500 $\mu$l injection (so the sonicate can have up to 40–100 mg of protein per ml).

ix) At this point the sonicate usually needs concentration in order to reduce the number of injections necessary to process the whole sonicate, and to increase the protein concentration to the allowable level. Concentrating is carried out using CENTRISART™ concentration tubes, with spins at 2500 rpm for 20 minutes each, at 4° C. The sonicate is usually concentrated in order to give 2 to 3×500 $\mu$l injections.

x) After concentration, the preparation is put down the MONO Q column in 500 $\mu$l injections. A readout is given for each injection and all parameters are recorded.

xi) Once the preparation has been run through the MONO Q fractions are checked for a urease peak.

xii) The values obtained from the urease test are plotted onto the protein profile obtained from the FPLC (see below). The required fractions are then pooled and a protein estimation performed. This protein concentration is used to determine the number of spins needed to concentrate the pool to approximately 1 ml. The preparation is concentrated using CENTRISART concentration tubes.

FPLC Antigenic Fractions i) Sonicate is further purified by fast protein liquid chromatography on a SUPEROSE™ 6 size exclusion column.

ii) The column is equilibrated with PBS pH 7.6–7.7 containing 0.02% w/v sodium azide.

iii) 200 $\mu$l of sonicate are loaded onto the column and 0.5 ml fractions collected.

iv) Fractions are collected and a urease test performed to find the urease peak. The values are plotted onto the readout obtained from the FPLC. The required fractions are pooled.

v) A small aliquot is taken to perform a native PAGE analysis to check consistency of bonding. These fractions do not include the urease peak but correspond to a peak representing a group of smaller proteins with molecular weights between 440 kDa and 67 kDa.

vi) The remainder is stored at $-20°$ C. and later pooled with other, similar preparations to form batches.

Freeze-Drying

Antigen from the above batches is freeze dried in an FSE Freeze Drier comprising:

(a) a Leybold (USA) TRIVAC™ pump, model No D4A;

(b) a General Electric (USA) 240 volt AC motor;

(c) a VIRTIS™ vacuum chamber (Virtis Co. Inc., New York, USA); and (d) a refrigeration unit incorporated into the cabinet of the freeze drier.

30 ml of antigen-containing liquid, frozen at an angle in a 5 cm diameter 50 ml specimen jar to increase surface area, was placed within the vacuum chamber, and the system operated. The temperature of the system in use was always set on $-55°$ C. The vacuum of the system in use was kept at 80–100 mTorr (approximately 0.001 atmospheres); the range value depends on the initial volume of frozen liquid and its surface area and, hence, the amount of vapour in the chamber. The sample was freeze-dried to complete dryness, which took 16–18 hours.

Native Gradient-PAGE using Pharmacia's PHASTSYSTEM™

Antigens from the above fractions, before and after freeze drying, are subjected to native PAGE using linear gradient acrylamide gels and the protein profiles visualised with rapid silver staining, as follows.

i) Buffer strips were PHASTGEL™ native buffer strips to separate proteins in their native state.

ii) The gel was PHASTGEL™ Gradient 8–25. This system gives a linear relationship between a protein's migration distance and the log of its molecular weight for the molecular weight range 50 kDa to 750 kDa for globular proteins.

iii) Markers used were Pharmacia's electrophoresis calibration kit for high molecular weight determinations. 1 vial (Cat. No. 17-0445-01) of lyophilised marker was dissolved in 100 $\mu$l distilled water. Reconstituted marker was diluted ⅒ for silver staining of gel. 1 $\mu$l marker was run in duplicate.

iv) For the antigen sample, 1 $\mu$l of each SUPEROSE™ 6 FPLC-purified extract was run in duplicate.

v) Separation conditions: samples were run using optimized method of native PAGE from PHASTSYSTEM™ Separation Technique File No. 120. The length of the run was 120 volt.hours.

vi) Development conditions: gel is silver stained following the method from Table 3 from PHASTSYSTEM™ Development Technique File No. 210 ("Silver Staining Method Optimised for Native-PAGE").

vii) The molecular weight determination is obtained using the high molecular weight markers that are run with the antigens on the gel. Standard curves are determined by plotting the log molecular weight against the $R_f$ value.

Comparison of Antigens before and after Freeze-Drying

Using the above native-PAGE methodology, the following results were obtained. Values are given as means plus or minus one standard deviation. (n) indicates the number of determinations that could be made from the gel.

|  | Purified | Freeze-dried |
|---|---|---|
| Antigen 1 | 436 ± 20.6 (4) | Not detected (4) |
| Antigen 2 | 338.6 ± 14.1 (4) | 334.0 ± 18.5 (4) |
| Antigen 3 | 248.0 ± 18.1 (4) | 262.0 ± 0 (2) |
| Antigen 4 | 162.7 ± 23.0 (3) | 162.0 (1) |
| Antigen 5 | 70.0 ± 0 (3) | 70.0 (1) |

Further Characterisation of Antigens i) Relative molecular masses may be estimated from standard containing thyroglobulin, ferritin, catalase, lactate dehydrogenase and albumin.

ii) Western blotting methods may be employed to detect the appropriate protein bands by using sera positive to *H. pylori*.

iii) FPLC fractionation removes those lower molecular weight bands which are reactive with negative sera.

iv) The effect of freeze drying on the antigen preparation appears to diminish the presence of a large molecular weight (about 440 kDa) unit which is reactive with false positive sera. The absence of the 440 kDa band is important in the discrimination between positive, false positive and negative sera.

The effect of this purification procedure is the identification of a protein in the molecular weight range 255–275 kDa but generally about 265 kDa and a protein whose molecular weight is about 340 kDa which are reactive to positive sera but not negative sera.

EXAMPLE 2

ENZYME-LINKED IMMUNOSORBENT ASSAY (ELISA)

1. Coating of ELISA Plates with Antigen
   i) Polystyrene ELISA plates are used (Polysorb, Nunc, Denmark).
   ii) Freeze dried antigen preparation from Example 1 is optimally diluted (highest dilution giving maximum sensitivity for antibody positive saliva without increasing reactivity of antibody negative saliva) in coating buffer (see 2(iii) below).
   iii) An aliquot of 100 µl of diluted antigen is added to "antigen" wells of an ELISA plate and 100 µl of coating buffer (without antigen) is added to "buffer" wells.
   iv) Plates are incubated overnight at 4° C. temperature.
   v) Incubated plates are emptied, an aliquot of 100 µl of 5% w/v dried skim milk powder/coating buffer (see 2(iii) below) added for 30 minutes and emptied immediately by flicking the contents out.
2. Buffers
   i) Phosphate buffered saline (PBS): 0.14M NaCl, 0.003M $Na_2HPO_4$, 0.001N $NaH_2PO_4.2H_2O$ in 1 liter of deionized water adjusted to pH 7.2.
   ii) Substrate buffer: 10.1 g citric acid, 14.2 g disodium hydrogen orthophosphate ($Na_2HPO_4$), 150 µl $H_2O_2$ (30% w/v) in 1 liter of deionized water adjusted to pH 5.0.
   iii) Coating buffer: 2.42 g TRIS[tris(hydroxymethyl) amino methane], 58.44 g NaCl, in 1 liter of deionized water adjusted to pH 7.5.
3. Treatment of Plates after Antigen Coating
   For long term storage (6 months) of antigen coated plates, plates are dried after coating and blocking and stored at 4° C. with a desiccant. This procedure is necessary for long term preservation of the antigen coated plates.
4. ELISA Procedure
   a) Horseradish peroxidase method
      i) An aliquot of 100 µl of saliva diluted ½ in 0.05% (w/v) dried skim milk powder/PBST (PBSTM) or 100 ul of saliva diluted ½ in PBSTM is added to an antigen well and to a buffer well of the ELISA plate.
      ii) Plates are incubated for up to 90 minutes at ambient temperature.
      iii) Plates are washed 5 times by immersion in PBST.
      iv) An aliquot of 100 µl of horseradish peroxidase anti-human IgG diluted optimally (highest dilution giving maximum sensitivity for antibody positive saliva without increasing reactivity of antibody negative saliva) in PBSTM is added to antigen and buffer wells.
      v) Plates are incubated for up to 90 minutes at ambient temperature.
      vi) Plates are washed 5 times by immersion in PBST.
      vii) An aliquot of 100 µl of horseradish peroxidase substrate (Product T-2885, Sigma, USA) in substrate buffer is added to antigen and buffer wells.
      viii) Plates are incubated for up to 30 minutes at ambient temperature.
      ix) 100 µl of 1M $H_2SO_4$ is added to antigen and buffer wells.
      x) For each serum or saliva sample, the absorbence (A) of the buffer well is subtracted from the A of the antigen well and the resultant A is converted to ELISA units using a standard curve (constructed from doubling dilutions of a standard antibody positive serum).
      xii) A survey of 100 saliva from patients who had been demonstrated by biopsy to be infected (or not infected) is used to determine the number of ELISA units corresponding to infection.

EXAMPLE 3

IMMUNOBLOTTING ASSAY

1. Preparation of *Helicobacter pylori* Antigen
   The procedure for the preparation of *H. pylori* antigen for the immunoblotting assay is identical to that in Example 1.
2. Coating of the Membrane with Antigen
   i) Nitrocellulose membrane is used. Nylon based membranes can also be used.
   ii) After blotting dry, the membrane is soaked for 5 minutes in an optimal dilution of antigen (highest dilution of antigen giving maximum sensitivity with antibody positive samples without producing positive reactions in antibody negative samples).
   iii) The membrane is then incubated for 30 minutes in 5% (w/v) skim milk powder/TBS.
   iv) The membrane is washed twice for 5 minutes in 0.05% (w/v) polyoxyethylene sorbitan monolaurate/TBS (TBST). For long term storage (up to 18 months) the membrane is then dried and stored at 4° C. with a desiccant.
   v) The membrane is immersed for up to 5 minutes in undiluted test saliva in a test bottle or under the tongue.

vi) The membrane is washed for 30 seconds under running tap water.

vii) The membrane is immersed in alkaline phosphatase-conjugated anti-human IgG optimally diluted (to enable distinction between antibody positive and antibody negative saliva) in PBSTM for up to 5 minutes.

viii) The membrane is washed for 30 seconds under running tap water.

ix) The membrane is immersed for 5 minutes in substrate (0.3 mg nitroblue tetrazolium, 0.15 mg 5-bromo-4-chloro-3-indolyl phosphate in 1 ml 0.1 M NaHCO$_3$, 1.0 mM MgCl$_2$, pH 9.8).

x) Antibody positive samples produce a mauve colour change in the antigen region of the membrane whereas antibody negative samples do not alter the colour of the membrane in the antigen region.

EXAMPLE 4

Patients referred to the Gastroenterology Department, Royal North Shore Hospital, NSW, for investigation of upper gastrointestinal symptoms were studied. Microbiological culture, microscopy for the detection of *H. pylori*, urease tests, and histology of gastric biopsies and ELISAs were performed on all patients where possible.

Correlation of Salivary Antibodies with Biopsy Tests for *H. pylori*

The relationship between gastric biopsy histology and saliva ELISA results together with other tests for *H. pylori* infection are shown in the following table.

A serum ELISA has been shown to be more sensitive and specific than the biopsy tests in detecting *H. pylori* infection and is becoming generally accepted as the "gold" standard for detection of *H. pylori* infections. The results in this table show that the salivary assay system performs equally as well as serum. Where no inflammation or chronic inflammation is present, all tests currently available, including urease, culture and histology, perform relatively equally. However, patients with active inflammation are indicated as having *H. pylori* infection more often with both the serum and salivary ELISA than with other systems. The reason for this may be the fact that the biopsy is a fairly random sampling procedure and may miss areas of *H. pylori* infestation. As can be seen the saliva ELISA results correlate well with the serum ELISA results.

| RELATIONSHIP BETWEEN ELISAs AND BIOPSY TESTS WITH GASTRIC HISTOLOGY | | | | | | | | | |
|---|---|---|---|---|---|---|---|---|---|
| Gastric | Serum | | Saliva | | CLO | | Culture | | Histology |
| Inflammation | − | + | − | + | − | + | − | + | − | + |
| NONE | 5 | 0 | 5 | 0 | 5 | 0 | 5 | 0 | 5 | 0 |
| CHRONIC | 3 | 1 | 3 | 1 | 3 | 1 | 3 | 1 | 3 | 1 |
| ACTIVE | 1 | 12 | 2 | 11 | 4 | 8 | 4 | 8 | 3 | 10 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

We claim:

1. A method for detecting contemporary infection by *Helicobacter pylori* in a mammal, the method comprising contacting a mucous secretion from the mammal with an antigen preparation from *H. pylori* for a time and under conditions sufficient for an IgG antibody in the mucous secretion specific to the antigen component to form a complex therewith and then subjecting the complex to a detecting means in order to detect the complex, wherein the antigen preparation comprises *H. pylori*-derived components of about 265 kDa and about 340 kDa and an *H. pylori*-derived component of about 440 kDa as determined by native PAGE has been removed.

2. A method as claimed in claim 1, wherein the antigen preparation additionally comprises *H. pylori*-derived antigen with molecular weights(s) of about 160 kDa and/or about 70 kDa.

3. A method as claimed in claim 2 wherein the mucous secretion is saliva.

4. A method as claimed in claim 1 wherein the mucous secretion is saliva.

5. A method as claimed in claim 1, wherein the antigen preparation is bound to a solid support.

6. A method as claimed in claim 5, wherein the solid support is a nitrocellulose strip.

7. A method as claimed in claim 1, wherein the detection means is a second antibody, conjugated with a reporter molecule, and which binds to *H. pylori*-specific antibody found in said secretion.

8. A method as claimed in claim 7, wherein the reporter molecule is an enzyme or fluorophore.

9. A method as claimed in claim 8, wherein the reporter molecule is an enzyme, and the enzyme is alkaline phosphatase.

10. A method as claimed in claim 1, wherein the mammal is a human.

11. A test kit for detecting *H. pylori* in mucous secretion of a mammal, said test kit comprising
    (a) a solid support having an antigen preparation of *H. pylori* immobilized thereon, wherein the antigen preparation comprises *H. pylori*-derived components of about 265 kDa and about 340 kDa and an *H. pylori*-derived component of about 440 kDa as determined by native PAGE has been removed; and
    (b) detection means which in use detect whether IgG in said mucous secretion binds to one or more components of the antigen preparation.

12. A kit as claimed in claim 11, wherein the antigen preparation additionally comprises *H. pylori*-derived antigen with molecular weight(s) of about 160 kDa and/or about 70 kDa.

13. A kit as claimed in claim 12, wherein the antigen is purified by FPLC chromatography.

14. A kit as claimed in claim 11, wherein the solid support is a nitrocellulose strip.

15. A kit as claimed in claim 11, wherein the detection means is a second antibody, conjugated with a reporter molecule, and which binds to *H. pylori*-specific antibody found in the secretion.

16. A kit as claimed in claim 15, wherein the reporter molecule is an enzyme or fluorophore.

17. A kit as claimed in claim 16, wherein the reporter molecule is an enzyme, and the enzyme is alkaline phosphatase.

18. A kit as claimed in claim 15, wherein the test kit is in compartment form and comprises:
    (a) a first compartment adapted to contain the solid support having an antigen preparation of *H. pyloriri* immobilized thereon;
    (b) a second compartment containing a second antibody conjugated with a reporter molecule capable of producing a signal, said second antibody being specific against IgG antibody; and (c) when the reporter molecule is an enzyme, a third compartment containing a substrate for said enzyme.

19. A kit as claimed in claim 18, further comprising additional compartments adapted to receive at least one of the assay components comprising mucous material, diluent and buffer.

20. An *H. pylori* antigen preparation comprising *H. pylori*-derived components of about 265 kDa and about 340 kDa and an *H. pylori*-derived component of about 440 kDa as determined by native PAGE has been removed.

* * * * *